(12) United States Patent
Wartman et al.

(10) Patent No.: US 10,548,697 B1
(45) Date of Patent: Feb. 4, 2020

(54) FLOSSER DISPENSER

(71) Applicant: One-Two, LLC, Chanhassen, MN (US)

(72) Inventors: Ryan Wartman, Chanhassen, MN (US); Chris Bollis, Orono, MN (US); Jeff Brown, Edina, MN (US)

(73) Assignee: One-Two, LLC, Chanhassen, MN (US)

( * ) Notice: Subject to any disclaimer, the term of this patent is extended or adjusted under 35 U.S.C. 154(b) by 0 days.

(21) Appl. No.: 16/555,503

(22) Filed: Aug. 29, 2019

(51) Int. Cl.
*B65D 1/00* (2006.01)
*A61C 15/04* (2006.01)
*B65D 6/06* (2006.01)

(52) U.S. Cl.
CPC .......... *A61C 15/043* (2013.01); *A61C 15/046* (2013.01); *B65D 11/12* (2013.01)

(58) Field of Classification Search
CPC .............................. B65D 11/12; A61C 15/046
USPC ................ 221/282–286, 197–198, 151–153, 221/303–310
See application file for complete search history.

(56) References Cited

U.S. PATENT DOCUMENTS

| 889,568 A * | 6/1908 | Albrecht | B65D 50/045 |
| | | | 206/1.5 |
| 2,450,635 A | 10/1948 | Dembenski | |
| 2,784,722 A | 3/1957 | Chamberlin et al. | |
| 3,519,004 A | 7/1970 | Foster | |
| 4,643,334 A | 2/1987 | Steele | |
| 4,807,752 A | 2/1989 | Chodorow | |
| 4,909,578 A | 3/1990 | Abbate | |
| 5,163,561 A | 11/1992 | Fitzgerald | |
| 5,275,291 A * | 1/1994 | Sledge | B65D 43/20 |
| | | | 206/1.5 |
| 5,620,109 A * | 4/1997 | Madden | B65D 11/12 |
| | | | 206/536 |
| 5,732,820 A | 3/1998 | Tsai | |

(Continued)

FOREIGN PATENT DOCUMENTS

| AU | 696781 B3 | 9/1998 |
| CN | 202051840 U | 11/2011 |

(Continued)

OTHER PUBLICATIONS

A-Titan; Dental Floss Dispenser, May 23, 2019; https://www.atitan.com/products/300-dental-floss-dispenser.

(Continued)

*Primary Examiner* — Timothy R Waggoner
(74) *Attorney, Agent, or Firm* — Grumbles Law PLLC; Brittany Nanzig

(57) ABSTRACT

A refillable flosser dispenser including a housing and a cover. The housing can include a dispensing body, a door attached to the dispensing body, and a multi-state actuator structured to alternate between compressed and extended positions. The interior space created by the dispensing body and the door is structured and configured to house flossers in a stacked orientation. The cover can include an open bottom and can fit over and around the housing, the cover having an interior shape larger than an exterior shape of the housing. By pushing the cover down, the user activates the multi-state actuator, which causes a bottom portion of the housing to be exposed so that the user can remove a single flosser at a time. The top and bottom halves of the housing are mirror images of each other and allow the dispenser to dispense from either end, thereby making the dispenser ambidextrous.

20 Claims, 9 Drawing Sheets

(56) References Cited

U.S. PATENT DOCUMENTS

| | | |
|---|---|---|
| 5,785,206 A | 7/1998 | Chan |
| 5,842,598 A | 12/1998 | Tsuchida |
| 5,873,495 A | 2/1999 | Saint-Germain |
| 6,158,615 A * | 12/2000 | Hill .................. A47F 1/10 221/154 |
| 6,488,036 B1 | 12/2002 | Francis |
| 6,971,546 B2 | 12/2005 | Costa |
| 7,036,664 B2 * | 5/2006 | Lee .................. B65D 75/366 206/1.5 |
| 7,654,273 B2 | 2/2010 | Grendol et al. |
| 8,297,473 B2 | 10/2012 | Smith |
| 9,265,593 B2 | 2/2016 | Stewart et al. |
| 9,655,703 B2 | 5/2017 | Studney |
| 9,994,344 B2 | 6/2018 | Buscema et al. |
| 2006/0091147 A1 | 5/2006 | Arndt |
| 2006/0289554 A1 | 12/2006 | Mitchell et al. |
| 2006/0289557 A1 | 12/2006 | Mitchell et al. |
| 2008/0295859 A1 * | 12/2008 | Grendol .............. A61C 15/043 132/324 |
| 2010/0084423 A1 * | 4/2010 | Zeitman .............. A61C 15/043 221/267 |
| 2010/0294791 A1 | 11/2010 | Weibel et al. |
| 2012/0234889 A1 | 9/2012 | Kim |
| 2016/0361147 A1 * | 12/2016 | Chodorow .......... A61C 15/043 |
| 2018/0334311 A1 | 11/2018 | Bittner |

FOREIGN PATENT DOCUMENTS

| | | |
|---|---|---|
| CN | 206403581 U | 8/2017 |
| CN | 107951583 A | 4/2018 |
| CN | 207429202 U | 6/2018 |
| FR | 2779700 A1 | 12/1999 |
| WO | 2005110890 A1 | 11/2005 |
| WO | 2018169823 A1 | 9/2018 |

OTHER PUBLICATIONS

Shenzhen Huicui Electronic Technology Co., Ltd; 32pack/lot Lit-Pack oral hygiene Toothpicks Dental Floss Picks Dental Flosser Tooth Pick; May 23, 2019; https://www.aliexpress.com/item/32box-lot-Lit-Pack-Toothpicks-Dental-Floss-Picks-Dental-Flosser-Tooth-Pick/871139112.html.

Plackers; Plackers Dental Flossers Mint; May 23, 2019; https://www.walgreens.com/store/c/plackers-dental-flossers-mint/ID=prod6016289-product.

* cited by examiner

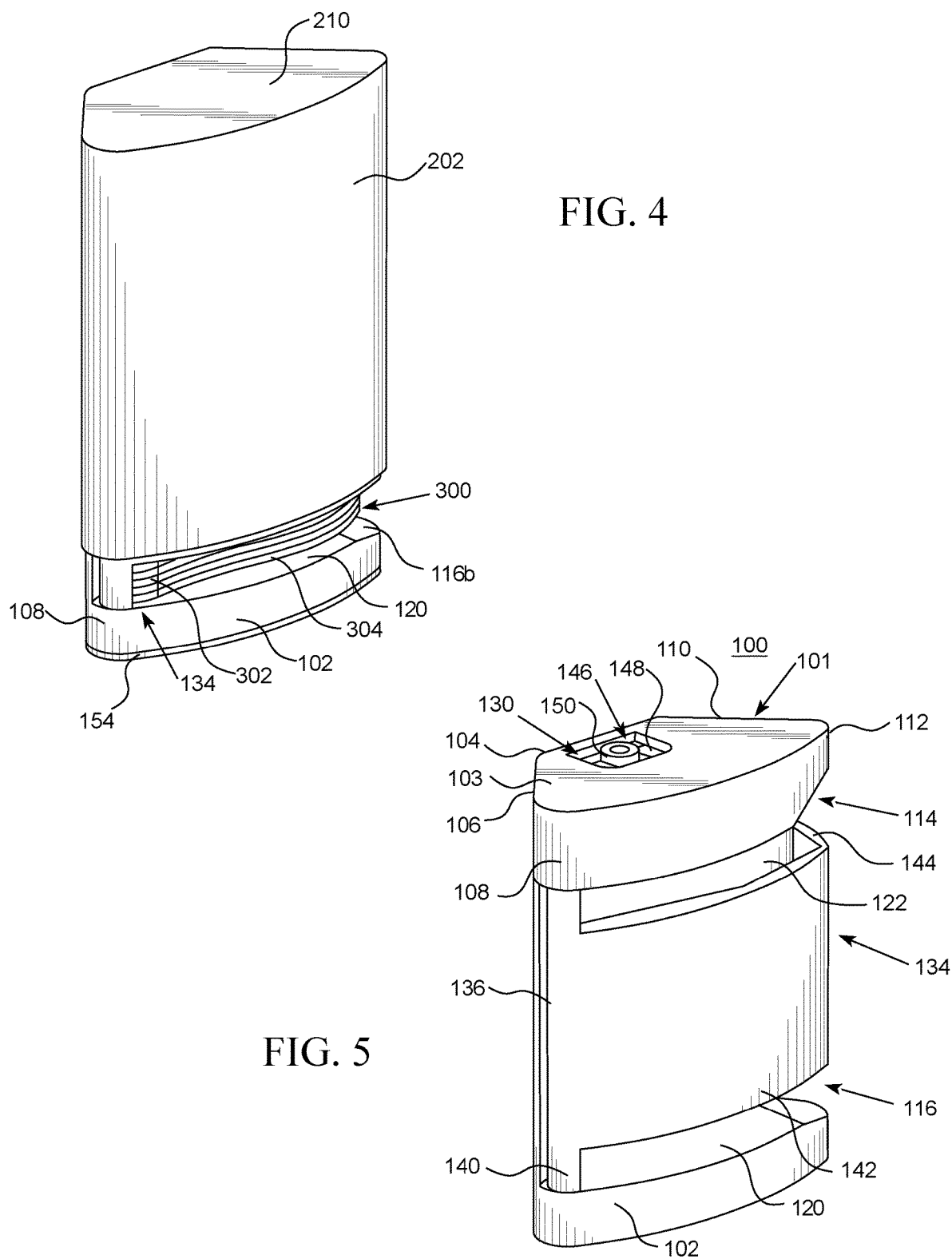

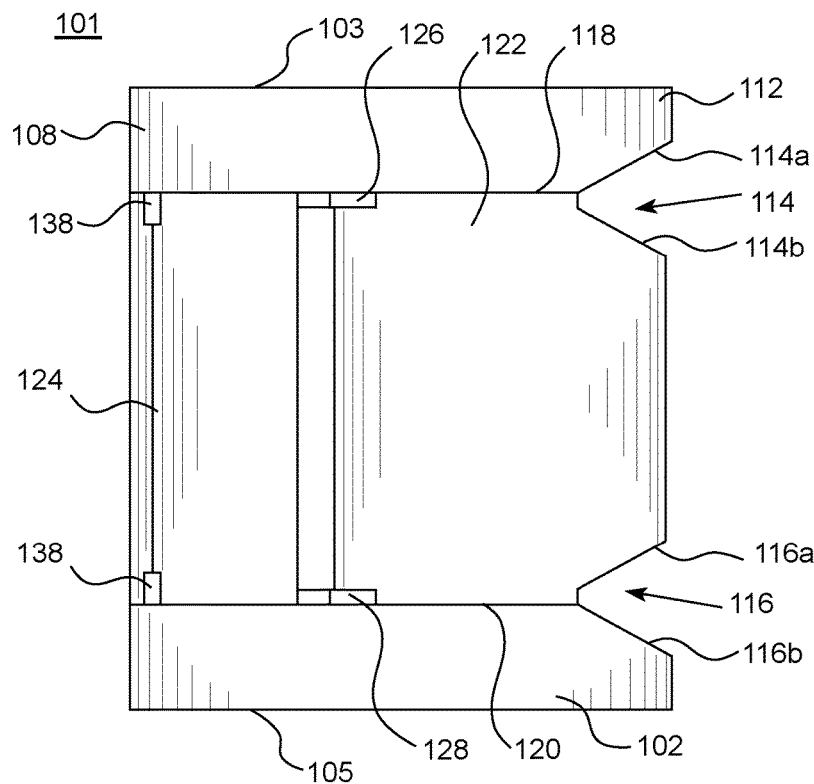
FIG. 14
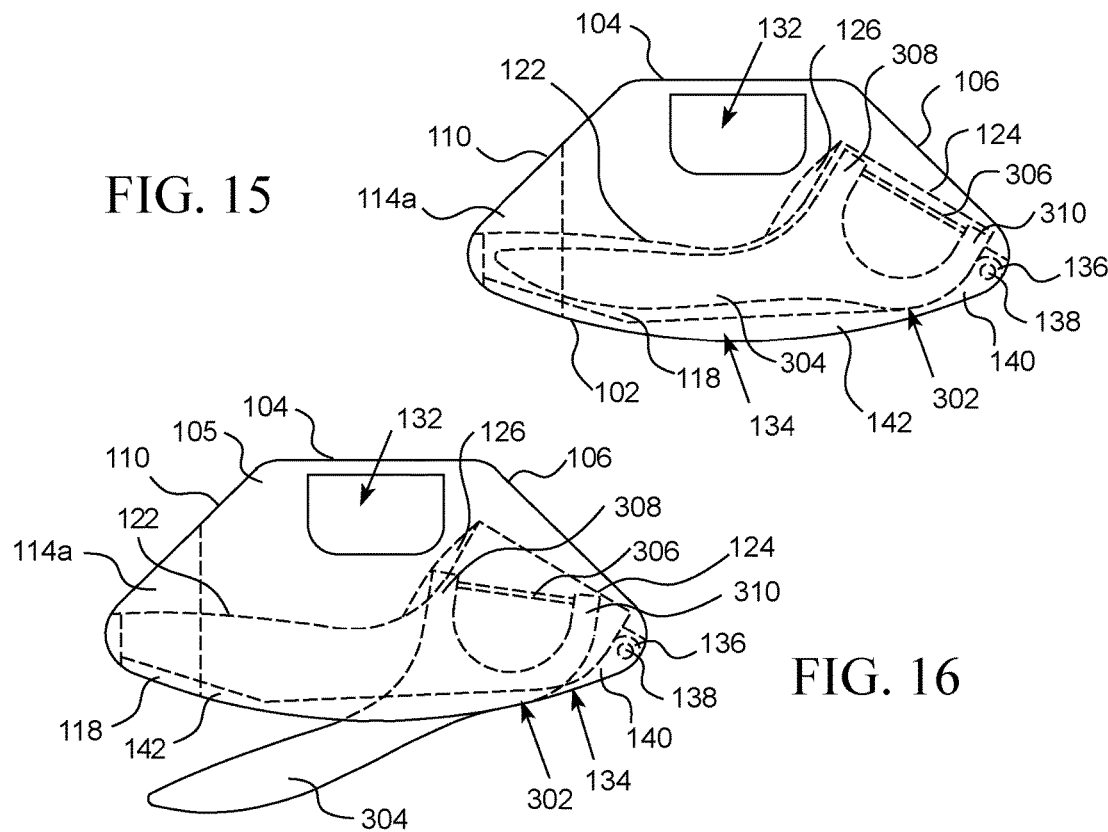
FIG. 15
FIG. 16

US 10,548,697 B1

FLOSSER DISPENSER

FIELD OF THE INVENTION

This disclosure relates to dispensers, and more particularly, relates to refillable dispensers for flossers.

BACKGROUND OF THE INVENTION

Dentists frequently inform individuals that they need to floss consistently. However, current flossing products, such as flossers and spooled floss, typically end up at the bottom of bathroom drawers, purses, and bags due to their small size. Further, buying a bag of flossers does not fix this problem, because they're not aesthetically pleasing, and flossers can be time-consuming to extract from them. Therefore, individuals lose motivation to floss due to the difficulty in storing and obtaining floss. A solution is needed that reminds individuals to floss and that makes the process of storing, obtaining and using floss easier and more sanitary.

SUMMARY OF THE INVENTION

This disclosure relates to dispensers, and more particularly, relates to refillable dispensers for flossers. In an illustrative but non-limiting example, the disclosure provides a flosser dispenser that can include a housing and a cover. The housing can include a dispensing body, a door attached to the dispensing body, and a multi-state actuator (for example, a touch latch), wherein the interior space created by the dispensing body and the door is structured and configured to house flossers in a stacked orientation. The cover can include an open bottom and can be structured and configured to have an interior shape larger than the exterior shape of the housing such that the cover fits over and around the housing. By pushing the cover down, the user activates the touch latch, which causes a bottom portion of the housing to be exposed so that the user can remove a single flosser at a time. The top and bottom halves of the housing are mirror images of each other and allow the dispenser to dispense from either end, thereby making the dispenser ambidextrous.

The above summary is not intended to describe each and every example or every implementation of the disclosure. The description that follows more particularly exemplifies various illustrative embodiments.

BRIEF DESCRIPTION OF THE DRAWINGS

The following description should be read with reference to the drawings. The drawings, which are not necessarily to scale, depict examples and are not intended to limit the scope of the disclosure. The disclosure may be more completely understood in consideration of the following description with respect to various examples in connection with the accompanying drawings, in which:

FIG. 4 is a front perspective view of the dispenser in an activated configuration, wherein the dispenser is housing flossers and has a base attached;

FIG. 5 is a front perspective view of the housing of the dispenser with the door closed;

FIG. 14 is a front view of the dispensing body;

FIG. 15 is a top view of the dispensing body with a flosser in the stored position, wherein the flosser is outlined with phantom lines;

FIG. 16 is a top view of the dispensing body with a flosser in the pivoting position, wherein the flosser is outlined with phantom lines;

DETAILED DESCRIPTION

Figure 1:
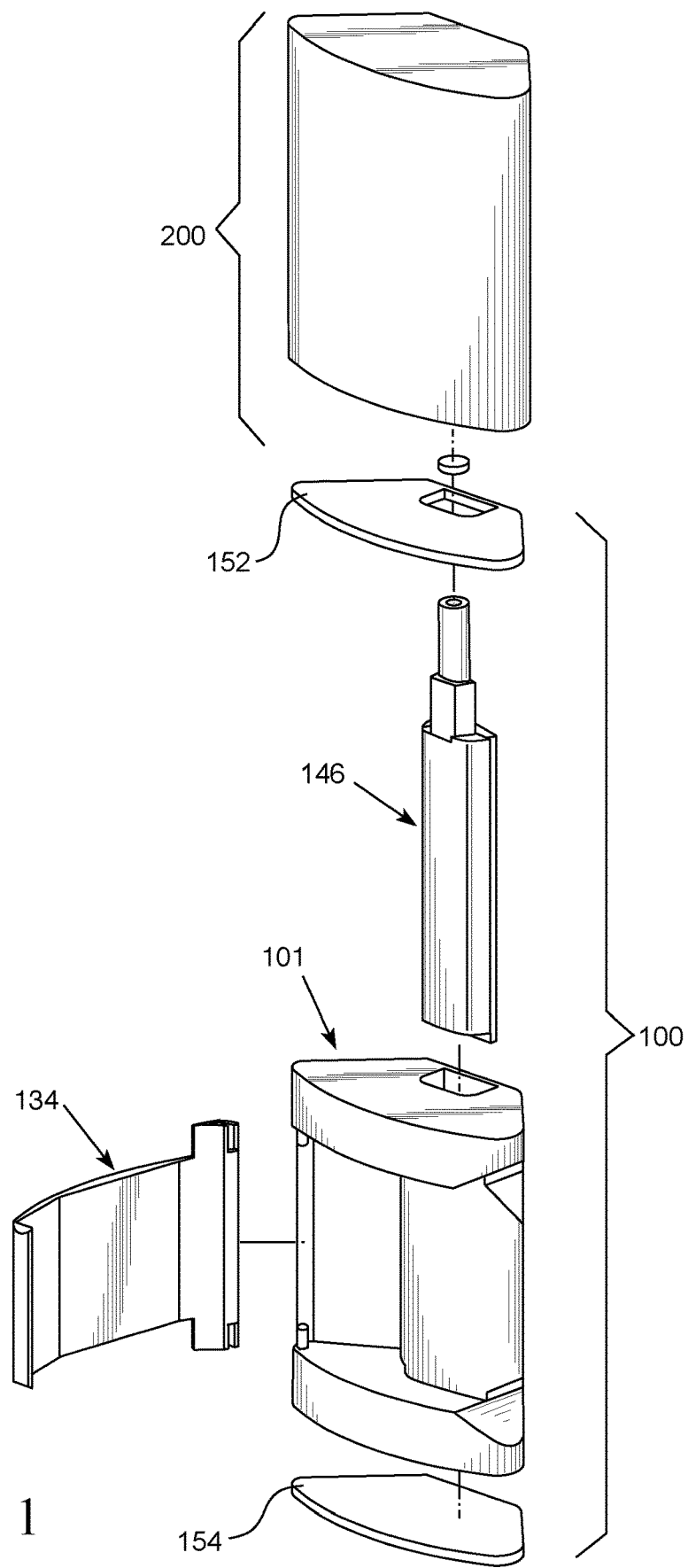
FIG. 1 is an exploded view of an illustrative example of a dispenser of the present disclosure.

The present disclosure relates to dispensers, and more particularly, relates to refillable dispensers for flossers. Various embodiments are described in detail with reference to the drawings, in which like reference numerals may be used to represent like parts and assemblies throughout the several views. Reference to various embodiments does not limit the scope of the systems and methods disclosed herein. Examples of construction, dimensions, and materials may be illustrated for the various elements; those skilled in the art will recognize that many of the examples provided have suitable alternatives that may be utilized. Any examples set forth in this specification are not intended to be limiting and merely set forth some of the many possible embodiments for the systems and methods. It is understood that various omissions and substitutions of equivalents are contemplated as circumstances may suggest or render expedient, but these are intended to cover applications or embodiments without departing from the spirit or scope of the disclosure. Also, it is to be understood that the phraseology and terminology used herein are for the purpose of description and should not be regarded as limiting.

Generally, the flosser dispenser described herein stores flossers in a stacked configuration and enables flossers to be removed one at a time from the bottom of the stack. More specifically, the disclosed device has a housing that houses flossers and that is substantially encased by a cover that prevents the dispensing body and enclosed flossers from coming into contact with moisture, dust, dirt, bacteria, etc. To access the flossers, a user can push the cover down to activate a multi-state actuator that pushes the cover partially up into an activated configuration. This exposes part of the housing including the dispensing portion. To remove a flosser, the dispensing body of the housing has a corner wedge cutout that exposes the tail end of a flosser and provides a gap in the body for a user to hook their finger behind the flosser and pull it forward. After a single flosser is removed, the stack moves downward due to gravitational forces. In some embodiments, the top half of the housing of the flosser dispenser is a mirror image of the bottom half. Therefore, the user can remove the cover entirely, flip the housing upside down, and replace the cover to use the device in a different handed configuration. As described herein, a right-handed configuration of the device has the above-referenced corner wedge cutout positioned on the right side of the device (when one is facing the front of the device) so that users can more easily use their right hand to withdraw a flosser. A left-handed configuration of the device has the corner wedge cutout position on the left side of the device so that users can more easily use their left hand to withdraw a flosser.

As referenced herein, dental flossers 300, also known as dental floss picks, generally include a head 302 and a handle 304. Often, the head includes a set of prongs with a piece of floss 306 strung between the tips of each prong. While handle 304 can be straight, more often it has curvature. Additionally, often times the handle attaches nearer to one prong versus centered on both prongs. Therefore, the prongs typically include a short prong 308 and a long prong 310 instead of two prongs of identical length.

In some embodiments, the flosser height can be defined as the distance between the top and bottom faces of a flosser at its thickest point, the faces of each flosser being the flat surfaces that are in contact with the flossers above and/or below the flosser when stacked together. Further, the flosser length can be defined as the distance between the tip of handle 304 and the tips of short and long prongs 308, 310, and the flosser width can be defined as the distance between the front and back edges of a flosser, although this distance is variable and depends on which portion of the flosser is being referred to.

In some embodiments, flossers 300 may be packaged together as a cartridge for easy refilling. For example, if housing 100 can accommodate up to 30 flossers, a cartridge may be prepackaged to contain up to 25 flossers so that the housing can be refilled while there are still a few remaining flossers in the housing, and the cartridge may be structured and configured to easily insert those flossers into the housing.

Figure 2:
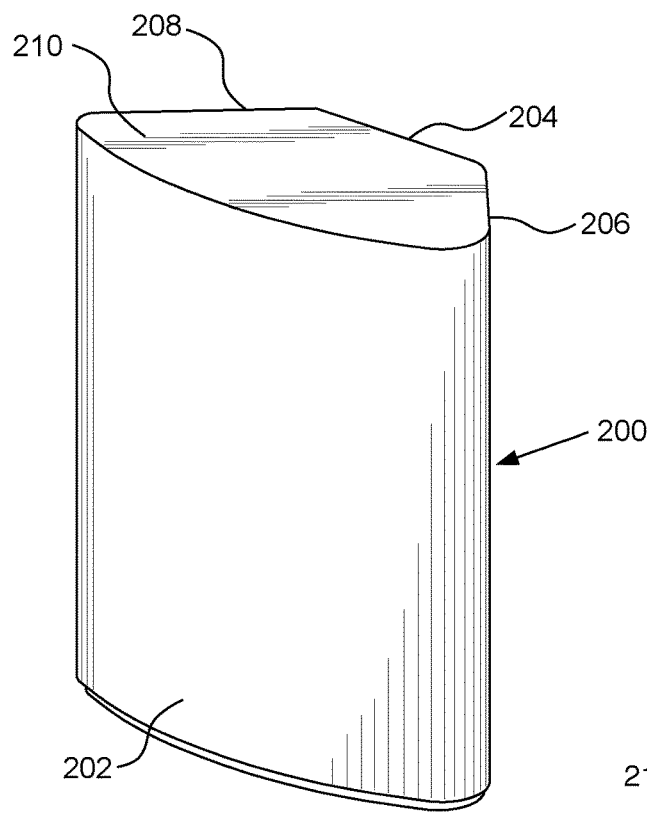
FIG. 2 is a front perspective view of the dispenser in a closed configuration.
Figure 3:
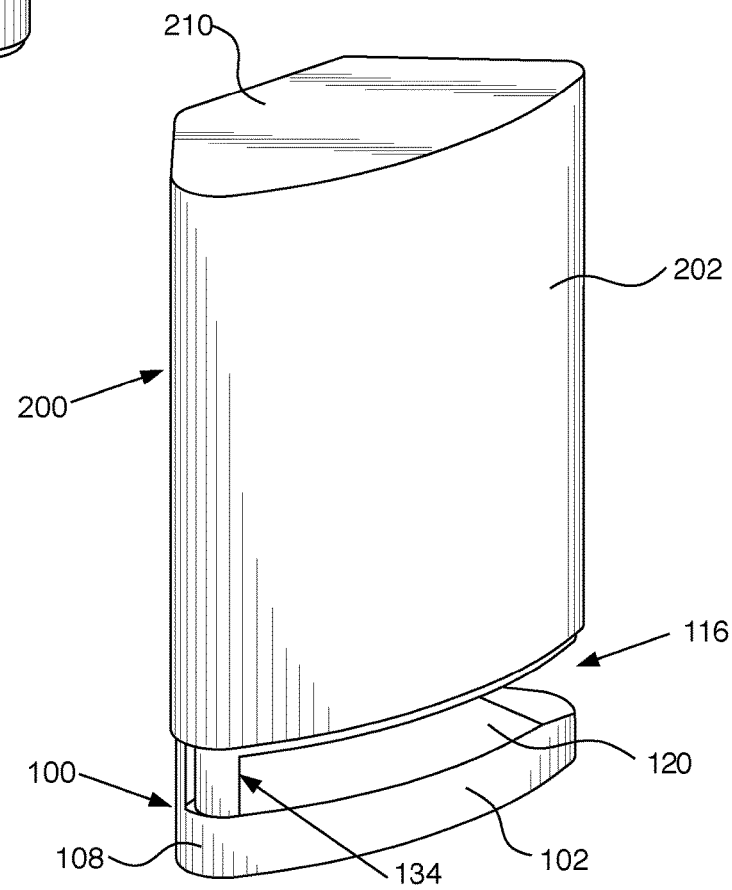
FIG. 3 is a front perspective view of the dispenser in an activated configuration.

FIG. 1 is an exploded view of an illustrative example of a dispenser. Generally, dispenser includes housing 100 and cover 200. Housing 100 can be comprised of dispensing body 101, door 134 attachable to the dispensing body, touch latch assembly 146, and in some cases, cap 152 and base 154, as illustrated in FIG. 1. Dispensing body 101 and door 134 can define an interior space that is structured and configured to house flossers 300 in a stacked orientation for individual removal. Cover 200 can be comprised of open bottom 212 and can be structured and configured to have an interior shape larger than the exterior shape of housing 100, such that the cover fits over and around the housing, as illustrated in FIG. 2. In some embodiments, dispensing body 101 has top cavity 130 and bottom cavity 132 (these may be one continuous cavity instead of two distinct cavities) into which touch latch assembly 146 can be inserted, thereby enabling the dispenser to be used in one of two positions, those two positions being the right-handed and left-handed positions, as described above. By pushing cover 200 down, the user activates touch latch assembly 146, which causes a bottom portion of housing 100 to be exposed so that the user can remove a single flosser from the dispensing body 101, as illustrated in FIGS. 3-4.

The flosser dispenser described herein is intended to encourage frequent flossing. Further, the structure and configuration of the dispenser makes it more suitable to be placed out in the open (e.g., bathroom countertops, dining tables or other living areas, cafeterias, dentist offices, restaurants, etc.) compared to existing flosser bags and containers, which merely provide an enclosed area with little to no organization and no means of dispensing the flossers. To maintain the sanitary nature of flossers 300 by preventing splashes and other debris from coming into contact with the flossers, cover 200 substantially encompasses housing 100 when the device is in its closed and stored configuration, as illustrated in FIG. 2. However, since touch latch assembly 146 is activated by downward force that causes release of a spring mechanism, a small area of the bottom portion of housing 100 can remain uncovered. This permits the touch latch assembly freedom to move slightly downward from its compressed position so it can be activated. Once activated, touch latch assembly 146 moves upward into an extended position and pushes cover 200 upward into a corresponding active configuration, as illustrated in FIG. 3. This action exposes a portion of housing 100 such that a plurality of flossers 300 are visible and accessible for dispensing, as illustrated in FIG. 4.

Figure 6:
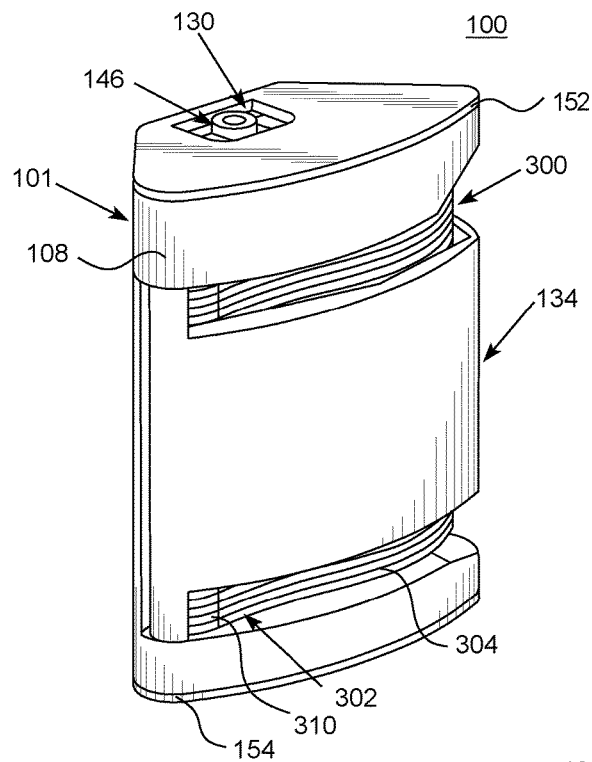
FIG. 6 is a front perspective view of the housing with the door closed, wherein the housing is housing flossers and has a cap and a base attached.

Housing 100 is rigid and can be generally comprised of dispensing body 101, door 134, and touch latch assembly 146, as illustrated in FIG. 5. As mentioned above, dispensing body 101 and door 134 can define an interior space that is structured and configured to house flossers 300 in a stacked orientation for individual removal, as illustrated in FIG. 6. More specifically, dispensing body 101 can be shaped similar to a trapezoid and include front face 102, top 103, back face 104, bottom 105, first side 106 having first front edge 108, second side 110 having second front edge 112. In some cases, housing 100 may also include cap 152 attached to top 103 and base 154 attached to bottom 105, as illustrated in FIG. 6.

Figure 7:
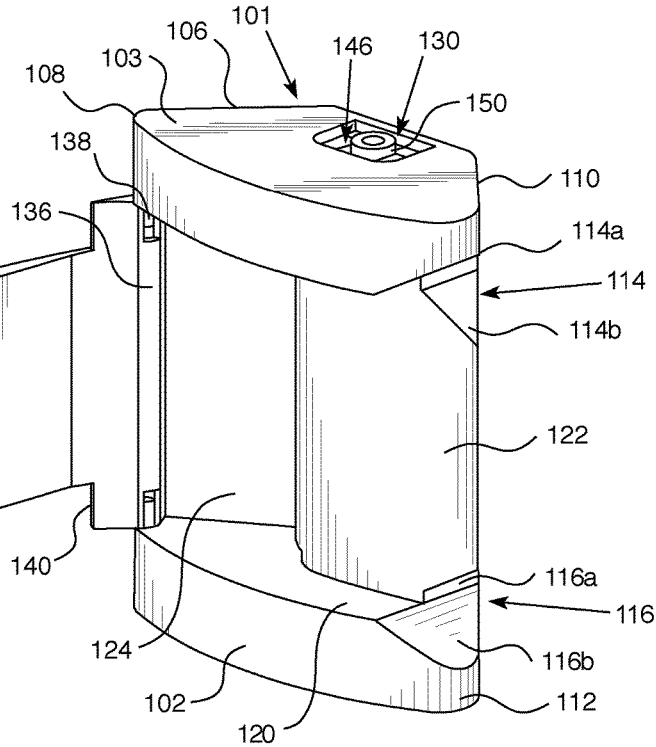
FIG. 7 is a front perspective view of the housing with the door open.
Figure 8:
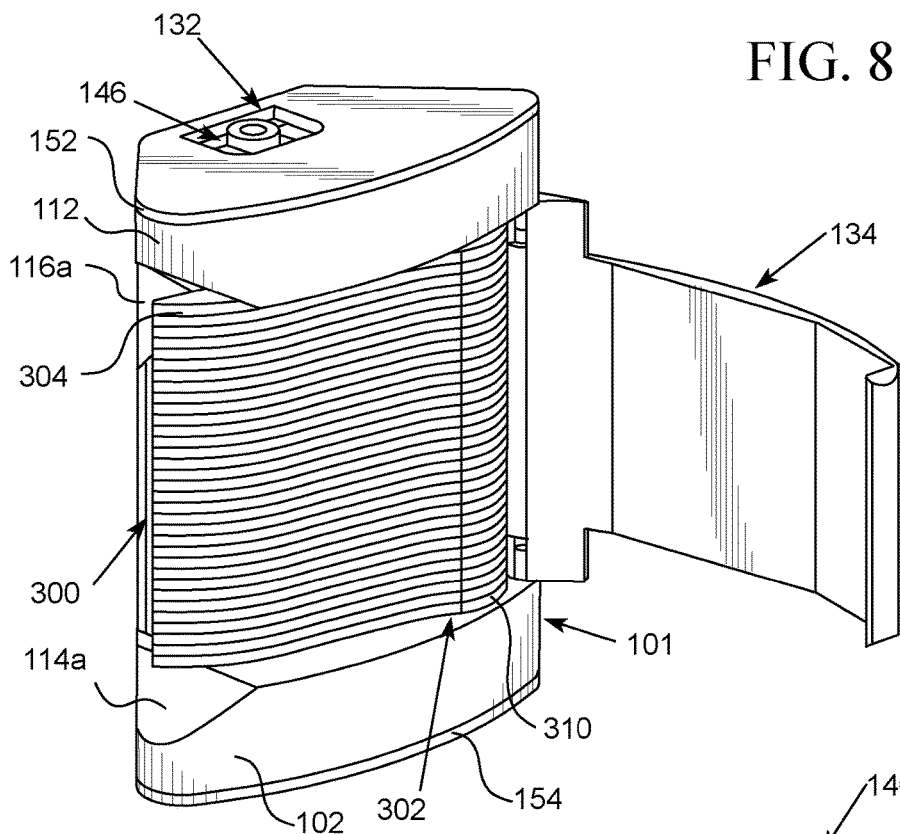
FIG. 8 is a front perspective view of the housing with the door open, wherein the dispenser is housing flossers and has a cap and a base attached.
Figure 9:
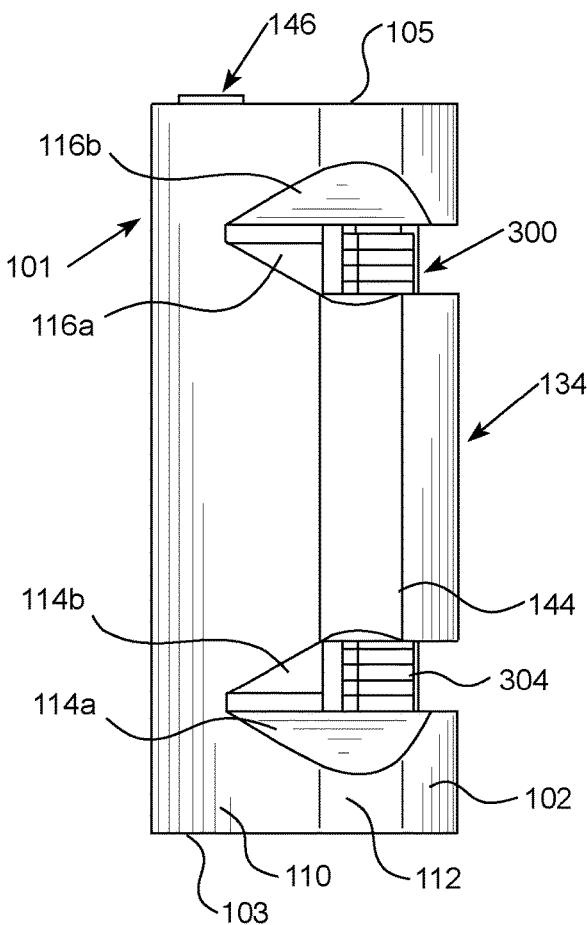
FIG. 9 is a side view of the housing with the door closed, wherein the dispenser is housing flossers.

Front face 102 can be relatively smooth, slightly curved outward, and can be primarily open so that flossers 300 can easily be loaded into dispensing body 101, as illustrated in FIGS. 7-8. As will be described herein, door 134 can cover a portion or a majority of front face 102, as illustrated in FIGS. 6 and 9, such that the open nature of the front face does not result in flossers 300 inadvertently falling out of dispensing body 101.

Figure 10:
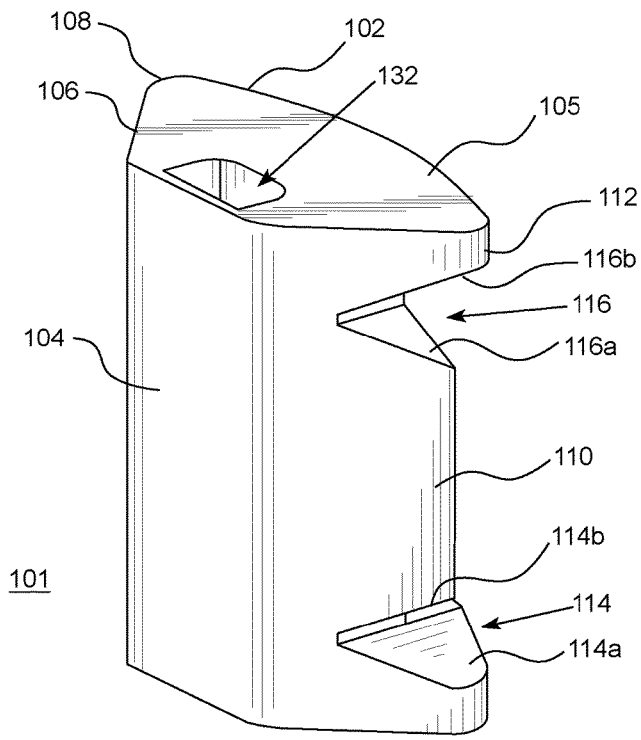
FIG. 10 is a back perspective view of the dispensing body of the housing.
Figure 11:
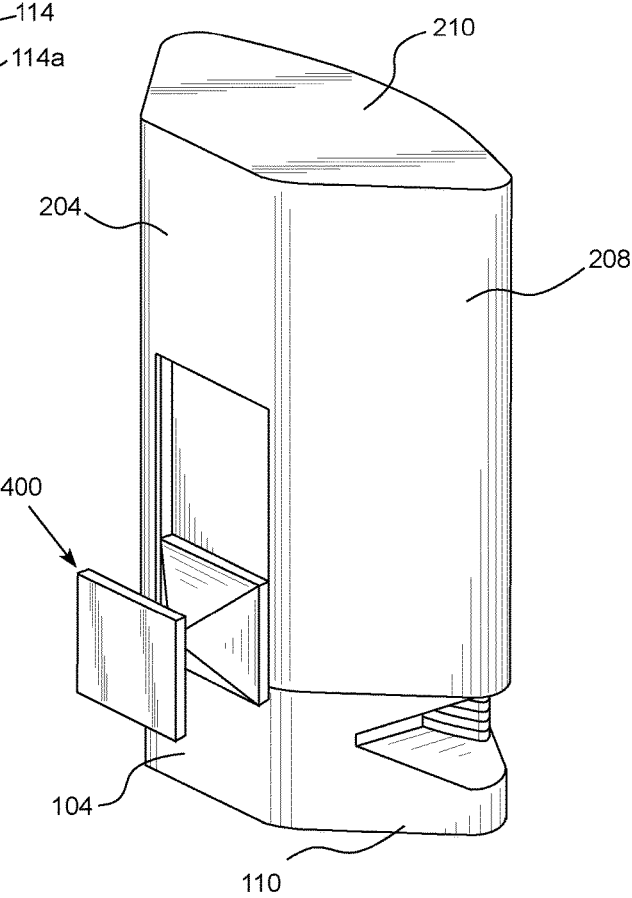
FIG. 11 is a back perspective view of the dispenser in an activated configuration, wherein the dispenser includes a wall mount.
Figure 12:
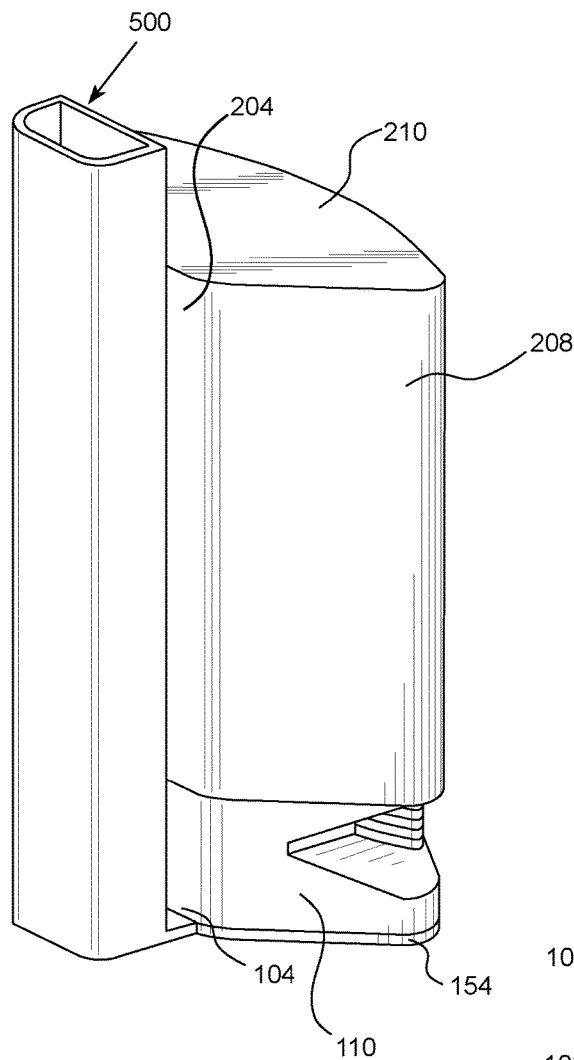
FIG. 12 is a back perspective view of the dispenser in an activated configuration, wherein the dispenser includes a toothbrush holder.

Back face 104 can also be relatively smooth, as illustrated in FIG. 10, and can provide a mounting surface onto which additional components attach. For example, mounting feature 400 can be attached to back face 104 to enable flosser dispenser to mount to a wall, as illustrated in in FIG. 11. Mounting hardware can be comprised of a suction cup, poster tape, screws, prongs for inserting into an electrical outlet, a magnet, etc. In another example, a storage feature, such as a toothbrush holder 500, can extend out the back of the device to enable flosser dispenser to replace common toothbrush storage in a bathroom, as illustrated in FIG. 12. However, the storage feature illustrated in FIG. 12 could also retain other items such as, but not limited to, pencils/pens, business cards, or used flossers. Further, instead of having an open top, the storage feature could be enclosed and could be a liquid soap dispenser or any other kind of liquid pump dispenser. Another item that can extend out the back of the device is a kick stand to assist with refilling by allowing housing 100 to lean backwards without tipping over.

Top 103 can be relatively smooth and flat and can include top cavity 130 inside which touch latch assembly 146 can be located, as illustrated in FIGS. 5-7. Bottom 105 can also be relatively smooth and flat and can include bottom cavity 132 inside which touch latch assembly 146 can be located, as illustrated in FIGS. 8-10. In some embodiments, top 103 and/or bottom 105 can have feet to increase the friction coefficient, prevent sliding, and make it easier for housing 100 to stay in place on a countertop or other surface when a user is removing flossers 300. Feet may be a plurality of sticky points or one single piece that covers a portion or all of bottom 105. Further, if housing 100 includes base 154, as described further below, the bottom surface of base may include the feet instead of bottom 105, since base will cover the bottom (or top 103, when the dispenser is configured in the left-handed configuration). Further, to prevent tipping, bottom 105, top 103, and/or base 154 may have added weights.

First side 106 and second side 110 can connect front face 102 to back face 104 at 45-degree angles, as illustrated in FIGS. 5-8 and 15-16. This enables flosser dispenser to be easily stored in a corner of a countertop such as, but not limited to, in a bathroom. First side 106, as described above, can have first front edge 108 along which door 134 can attach, as illustrated in FIG. 7. Second side 110, as described above, can have second front edge 112, which itself has upper wedge cutout 114 and lower wedge cutout 116, as illustrated in FIG. 7, which expose handles 304 of flossers 300, as illustrated in FIGS. 8-9 and 11-12. The upper and lower wedge cutouts can be any shape such as, but not limited to, a traditional pyramidal wedge shape, a rectangular cuboid, or a cube and may be mirror images of each other. In some embodiments, upper wedge cutout 114 and lower wedge cutout 116 are approximately 55-degree angle wedges, as illustrated in FIG. 9, although they may be greater or smaller angles.

Upper wedge cutout 114 can be located along second front edge 112 at the intersection of the second front edge and the top of the open area of front face 102, as illustrated in FIG. 7. More specifically, upper wedge cutout 114 may be comprised of upper wedge top portion 114*a* and upper wedge bottom portion 114*b* and may be horizontally aligned with top interior surface 118 (i.e., a ceiling) such that the upper wedge top portion may be above the plane of the top interior surface and closer to a top exterior surface of dispensing body 101, and the upper wedge bottom portion may be below the plane of the top interior surface and closer to the horizontal center line of the dispensing body, as illustrated in FIG. 9.

Similar to upper wedge cutout 114, lower wedge cutout 116 is also located along second front edge 112 but is at the intersection of the second front edge and the bottom of the open area of front face 102, as illustrated in FIG. 7. More specifically, lower wedge cutout 116 may be comprised of lower wedge top portion 116*a* and lower wedge bottom portion 116*b* and may be horizontally centered on bottom interior surface 120 (i.e., a floor) such that the lower wedge top portion may be above the plane of the bottom interior surface and closer to the horizontal center line of dispensing body 101, and the lower wedge bottom portion may be below the plane of the bottom interior surface and closer to a bottom exterior surface of the dispensing body, as illustrated in FIG. 9.

In some embodiments, housing 100 may further be comprised of a cap and a base that are located on the top and bottom of the dispenser, respectively (although, as noted below, "top" and "bottom" may be relative due to the ability of the dispenser to operate in either of the right- or left-handed configurations). More specifically, cap 152 and base 154 may be removable and may be placed on either top 103 or bottom 105, depending on whether the dispenser is in the right- or left-handed configuration. For example, in the right-handed configuration, cap 152 can be placed on top 103, and base 154 can be placed on bottom 105. In the left-handed configuration, the opposite is true: cap 152 can be placed on bottom 105, and base 154 can be placed on top 103. Since both cap 152 and base 154 are removable, they can incorporate a securing feature such as a rib(s), that enables them to stay in place once attached. For example, cap 152 and base 154 may include a rib that runs along the interior perimeter, and top 103 and bottom 105 may include a track that runs along a corresponding region of the exterior perimeter of the top and bottom. Therefore, the interior rib of cap 152 or base 154 can align inside the track of top 103 or bottom 105 to hold the cap and base in place. Further, cap 152 and base 154 may include one or more minor cutouts along their edge (for example, a front corner) to enable a user to more easily remove them from the top and bottom of housing 100.

Figure 13:
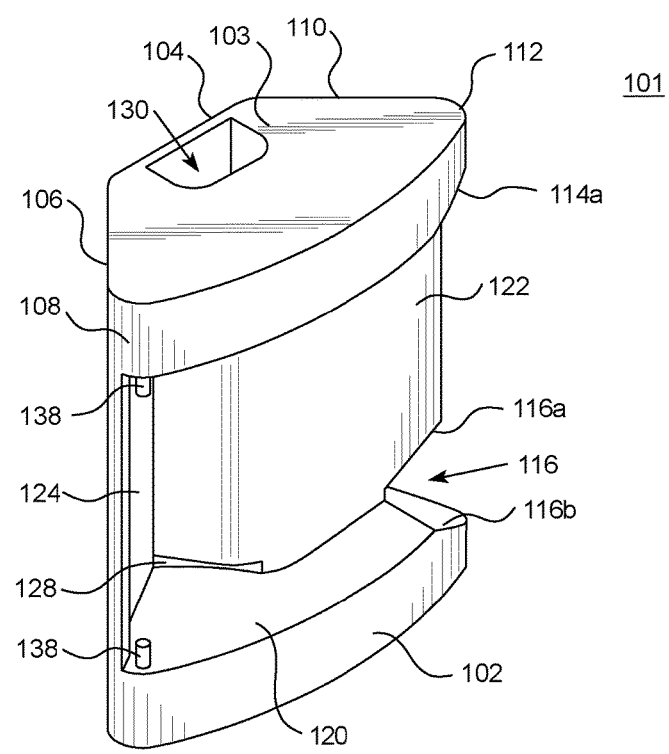
FIG. 13 is a front perspective view of the dispensing body.

In addition to the exterior features of dispensing body 101 described above, additional interior features may include top interior surface 118, bottom interior surface 120, interior back wall 122, interior side wall 124, top layer interior groove 126, and bottom layer interior groove 128, as illustrated in FIGS. 13-14. Top interior surface 118, bottom interior surface 120, interior back wall 122, and interior side wall 124 can be structured and configured to define a space wherein flossers 300 can be housed in a stacked orientation, as illustrated in FIGS. 8 and 15-16. More specifically, interior back wall 122 can be shaped to substantially align with head 302 and handle 304 of flosser 300 on the short prong 308 side of the flosser, and interior side wall 124 can be shaped to substantially align with head 302, such that floss 306 runs parallel to the interior side wall, as illustrated in FIG. 15.

The number of flossers 300 that could be housed within the flosser dispenser can vary. For example, a standard flosser dispenser may be sized to house 30 flossers, whereas a miniaturized version may be sized to house 10 flossers and may more easily fit in, for example, the center console of a car, within a purse, or within a small bag and, therefore, function as an on-the-go option for a flosser dispenser.

It is anticipated that flossers 300 are gravity-fed (i.e., as the bottom-most flosser is removed, the next flosser will be forced into the bottommost position due to the forces of gravity) and, therefore, do not require additional mechanics, such as spring mechanics, to progress the next flosser into dispensing position. However, an internal cavity spring or any other compressible material may be included, which could help prevent jamming of flossers by holding them in place more securely than what is allowed by the combination of gravity and space within housing 100.

Top interior surface 118 and bottom interior surface 120 can both be flat surfaces upon which flossers 300 can stack. The surfaces of top interior surface 118 and bottom interior surface 120 can be horizontal, as illustrated in FIGS. 9 and 14. Alternatively, top interior surface 118 and bottom interior surface 120 can be at slight angles so as to retain flossers 300 in their stacked configuration when door 146 is opened. Further, the shape of top and bottom interior surfaces 118, 120 can reflect the overall outline of flossers 300 and can be defined by interior back wall 122 and interior side wall 124, as illustrated in FIG. 13. More specifically, starting near second front edge 112, interior back wall 122 runs roughly parallel to front face 102. At around the center point of front face 102, interior back wall 122 curves back toward back face 104 so as to create a larger area in which flosser head 302 can fit. Interior back wall 122 then terminates near a back corner of first side 106 and in contact with interior side wall 124, which runs roughly parallel to the first side. Interior side wall 124 can therefore run from first front edge 108 and along first side 106 to the back corner of the first side.

Figure 17:
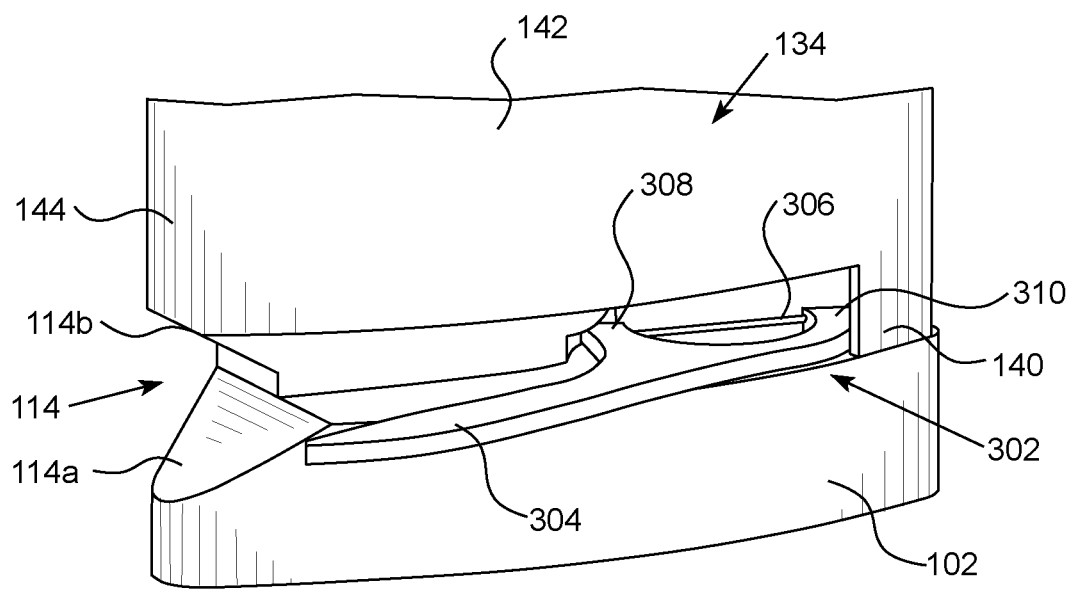
FIG. 17 is a front perspective view of a bottom portion of the housing with a flosser in the pivoting position.

At the intersection of interior back wall 122, interior side wall 124, and top interior surface 118 is where top layer interior groove 126 begins. Similarly, at the intersection of interior back wall 122, interior side wall 124, and bottom interior surface 120 is where bottom layer interior groove 128 begins. More specifically, each of top and bottom layer interior grooves 126, 128 cut into interior back wall 122, as illustrated in FIGS. 13-14, so as to create a curved groove in the back wall near short prong 308 of flosser head 302. Therefore, top layer interior groove 126 and bottom layer interior groove 128 are mirror images of each other about the center horizontal plane. The depth and length of interior grooves 126, 128 are such that they enable short prong 308 to rotate from a stored position through the grooves, as illustrated in FIGS. 16-17. While the depth and length have a minimum measurement to enable rotation of flosser 300, there is no known maximum and the grooves 126, 128 can be deeper and longer than needed to accommodate the length of short prong 308. Further, the height of interior grooves 126, 128 is greater than the height of a single flosser 300 and less than the height of two flossers, such that only one flosser at a time can fit into either of the interior grooves. The configuration of top and bottom interior grooves 126, 128 therefore enable a user to extract a single flosser 300 at a time when housing 100 is in either a right- or left-handed configuration. For example, as illustrated in FIGS. 15-16, a single flosser (indicated with phantom lines in FIGS. 15-16) can pivot through the top layer interior groove 128 (also indicated with phantom lines in FIGS. 15-16) when the dispenser is in the left-handed configuration.

In addition to exterior and interior features, dispensing body 101 may also be comprised of an opening or cavity in which an activation mechanism for cover 200 can be located. For example, top cavity 130 and bottom cavity 132 may house touch latch assembly 146 such that the touch latch assembly is encompassed within a surrounding space, as illustrated in FIGS. 5-9. In some embodiments, top cavity 130 and bottom cavity 132 may be two distinct cavities in dispensing body 101 such that there is a solid layer between the two cavities. In other embodiments, top and bottom cavities cavity 130, 132 may be one continuous cavity that is a through hole in dispensing body 101. However, while top and bottom cavities 130, 132 are illustrated as being fully encompassed within dispensing body 101, they do not necessarily need to be fully encompassed. For example, they may be insets along back face 104. In the case of insets, touch latch assembly 146 may be attached to insets via a magnet, snap fit, screw, ribs/tracks, adhesive, etc.

As described above, one embodiment of the flosser dispenser includes a cap and base for housing 100. One of the benefits of cap 152 and base 154 is that they can operate to retain touch latch assembly 146 within top and bottom cavities 130, 132. Therefore, if a user wishes to switch the flosser dispenser from a right-handed configuration to a left-handed configuration, the user can remove cover 200 from housing 100; remove cap 152 and base 154 from top 103 and bottom 105, respectively, by, for example, hooking a fingernail, flosser, coin, or other tool under the minor cutouts and pulling on them; remove touch latch assembly 146 from top cavity 130; flip housing 100 upside down; attach base 154 to top 103; insert touch latch assembly 146 into bottom cavity 132; attach top 152 to bottom 105; and place cover 200 back over housing 100. The reverse is true if a user wishes to switch the flosser dispenser from a left-handed configuration to a right-handed configuration.

In addition to dispensing body 101, housing 100 can include door 134. Door 134, as described above and illustrated in FIGS. 5-8, can connect at or along first front edge 108 and can be comprised of a first connection component, which can attach to a door connection on dispensing body 101, and a door cover component. Connection component can be, for example, door hinge 136, which is located along a first side edge of door 134, and door connection can be hinge pins 138, which are located near first front edge 108 of dispensing body 101, as illustrated in FIGS. 7-8. Therefore, door hinge 136 can attach to hinge pins 138, and door 134 can rotate around this connection point so that the door swings open and closed for loading of flossers 300, as illustrated in FIGS. 5-8.

In some embodiments, door 134 may have a second connection component at or along a second side edge of the door that attaches to, or makes contact with, dispensing body 101 near, for example, second front edge 112. This second connection component may be door handle 144, although the door handle may also be a standalone component and not necessarily a second connection component. Door handle 144 may latch or lock onto dispensing body 101 or, alternatively, the door handle may rest against the dispensing body and, therefore, be held in place when cover 200 is placed over the dispensing body. In another example, first and second connection components may snap onto dispensing body 101, for example, on front face 102 or at first and second front edges 108, 112. While the above-described connection means have been described, other connection means are envisioned.

For example, in another embodiment, door 134 may have a second connection component at or along a first side edge of door hinge 136 and along first front edge 108. For example, an inner surface of first front edge 108 may have an elongate latching rib running up and down, and an outer surface of hinge 136 on door 134 may have a corresponding latching rib running up and down such that when the door is rotated into a closed position, the latching rib on the hinge flexes and snaps over and past the latching rib on the first front edge (which may alternatively, or additionally, flex) and into a locked position. This locked position of the latching ribs prevents door 134 from inadvertently opening if cover 200 is removed from housing 100, and the housing is tilted forward.

As described above, another component of door 134 can be a door cover component that covers a portion or a majority of front face 102 thereby helping to retain flossers 300 in their desired stacked configuration, prevent flossers from inadvertently falling out of dispensing body 101, and, in some embodiments, prevent more than one flosser from being removed at a time. For example, the cover component can include vertical side portion 140 and horizontal portion 142, as illustrated in FIGS. 5-6.

Vertical side portion 140 can extend completely from top to bottom of the open area of front face 102 so that all flossers 300 are covered by the vertical side portion. Vertical side portion can be positioned next to door hinge 136 and, therefore, near first front edge 108 so that it covers at least a portion of flosser heads 302. This positioning allows vertical side portion 140 to prevent flossers 300 from inadvertently falling out of dispensing body 101 and allows only the lowest positioned flosser to be rotated through the interior groove 126 or 128. For example, in a left-handed configuration, the flosser directly in contact with top interior surface 118 (i.e., the flosser that is at the bottom of the stacked group of flossers) is the only flosser that can rotate through top layer interior groove 126, as illustrated in FIGS. 15-17. The opposite is also true in a right-handed configuration, wherein the flosser directly in contact with bottom interior surface 120 is the only flosser that can rotate through bottom layer interior groove 128.

Horizontal portion 142 can extend from a central part of the interior edge of vertical side portion 140 across the open area of front face 102 and toward second front edge 112. Horizontal portion 142 can terminate either in the open area of front face 102 or it can extend all the way across and terminate at second front edge 112, as illustrated in FIGS. 5-6. For example, horizontal portion 142 may terminate at door handle 144. Additionally, the height of horizontal portion 142 is less than that of vertical portion 140 and of the open area of front face 102. For example, horizontal portion 142 may have a height that is at least two flosser heights less than the height of the open area of front face 102, and the horizontal portion may be centered on the open area of the front face so as to allow a space large enough at the top and bottom of the front face for a flosser to rotate through. In some embodiments, horizontal portion 142 may have an even smaller height such that a plurality of flosser handles 304 are visible at the top and bottom of the stacked configuration when door 134 is closed and a full set of flossers have been loaded, as illustrated in FIG. 6.

As illustrated in FIGS. 15-16, the combination of door 134, interior back wall 122, and interior side wall 124 can define a space in which a stack of flossers 300 can fit on their top and bottom faces (which face is dependent upon whether the device is in the right- or left-handed configuration). Additionally, the distance between the edges of flossers 300 and each of door 134, back wall 122, and side wall 124 are minimal so as to prevent flossers 300 from excess movement that would cause them to rotate into a non-stacked configuration within dispensing body 101.

As described above, in addition to dispensing body 101 and door 134, housing 100 can include multi-state actuator, such as touch latch assembly 146 (also known as a push latch). Touch latch assembly 146, as briefly described above, can be a spring activated bi-state actuator such that, in a first, closed state, the touch latch is compressed into a shorter height than its height in a second, open state where the touch latch is expanded in height. In some embodiments, pushing down on touch latch assembly 146 causes it to move between these two states. In other embodiments, activation of the multi-state actuator may occur using functions such as, but not limited to, motion activation, voice activation, a push button located on top of cover 200, etc. Therefore, pushing down on touch latch assembly 146 or otherwise activating the multi-state actuator can move it from the first, closed state to the second, open state. Further, pushing down on touch latch assembly 146 or otherwise activating the multi-state actuator when it is in the second, open state will move it back to the first, closed state.

More specifically, in some embodiments, touch latch assembly 146 can include at least latch base 148 and latch extension 150. Latch base 148 can house latch extension 150 and can be located, as described above, within top and/or bottom cavities 130, 132, as illustrated in FIGS. 1 and 5-8. Latch base 148 can also house a spring (not shown), which can be in line with latch extension 150 such that, when the latch extension is pushed down, it makes contact with the spring and further compresses the spring. The spring then stores energy so that when latch extension 150 is pushed down on again, the spring forces the latch extension to extend upward. As illustrated in FIG. 9, touch latch assembly 146 may extend slightly above bottom 105 of dispensing body 101 when the device is in the left-handed configuration. Similarly, in the right-handed configuration, touch latch assembly 146 may extend slightly above top 103 of dispensing body 101. This provides space for touch latch assembly 146 to be compressed slightly from the first, closed state so as to release it into the second, open state. Touch latch assembly 146 can, in some cases, be partially or entirely magnetic or can be comprised of ferromagnetic materials. For example, a top portion of latch extension 150 may be ferromagnetic or may include a magnet while the remainder of touch latch assembly 146 is plastic.

Figure 18:
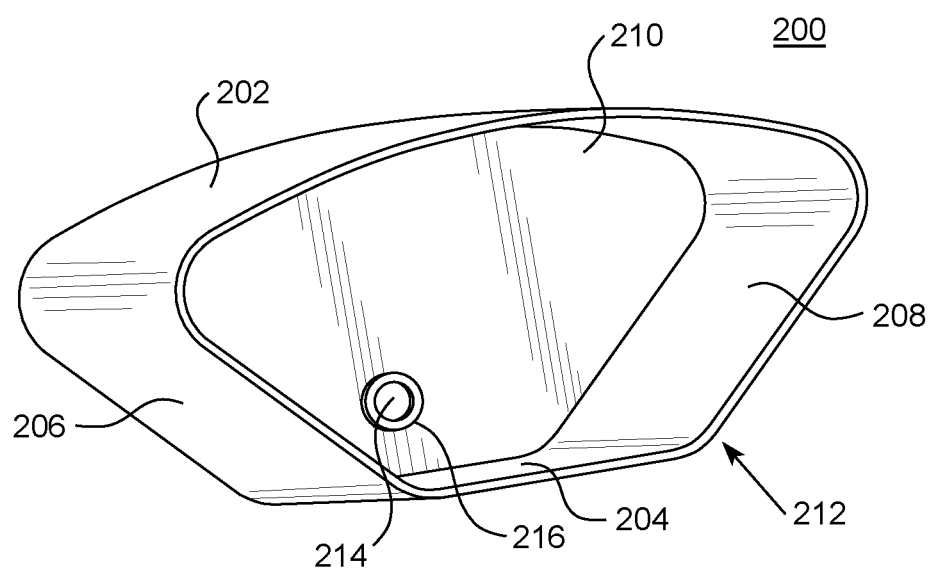
FIG. 18 is a bottom perspective view of the cover of the dispenser.

Cover 200, as described above, is intended to prevent flossers 300 from unsanitary conditions such as splashed or spilled water, etc. It can have a front wall 202, back wall 204, first side 206, second side 208, and top 210, as illustrated in FIG. 2. The external shape of cover 200 can have any type of external shape to aid in marketing of the flosser dispenser, as described further below. Further, cover 200 can have open bottom 212, as illustrated in FIG. 18, which enables it to slide over and around housing 100 and which, in combination with the overall shape of the cover, can create a snug fit if the interior shape of cover 200 is substantially equivalent to the exterior shape of housing 100. However, the interior shape of cover 200 does not need to be substantially equivalent to the exterior shape of housing 100, and it may instead merely be larger and of a different shape. While the external shape of cover 200 can vary, the cover may fit best if the internal shape is substantially similar to the external shape of housing 100.

The interior surface of cover 200 can be smooth, such that it slides easily over the housing when transitioning between closed and activated configurations and when the cover is removed from the housing. Alternatively, the interior surface of cover 200 may have materials overlaid, embedded, or inset in the surface such as felt or vinyl. In another embodiment, instead of having additional materials added to the interior surface, cover 200 may include ribs incorporated into the mold. These ribs may run longitudinally (for example, from top to bottom) or they may run horizontally (for example, from side to side).

Cover 200, as described above, is removable and can be made of any rigid material such as, but not limited to, plastic, wood, or metal (for example, stainless steel or anodized aluminum). In some embodiments, the bottom portion of front wall 202 can be chamfered near its front edges to enable cover 200 to drag a second flosser back inside housing 100 if the first flosser, when being removed by a user, pulls on the second flosser to move it forward and slightly out of place. Further, front wall 202 can be curved and can have a uniform texture (for example, smooth) so as to make it easy for adding and viewing images on the surface (for example, advertisements, decorative graphics, marketing content, etc.). These can be incorporated into cover 200 itself during the manufacturing process, or they can be added via adhesives, shrink wrap, glue, etc. Additionally, at least front wall 202 of cover 200 can have enhanced features such as: a dry-erase or chalkboard finish to enable users to draw on the cover; a one-time customizable surface that allows users to permanently paint, draw, or color their dispensers; a digital calendar; a digital screen; a clock; a night light; a photo insert; and a magnetic surface that allows users to attach magnetic objects to the dispenser. In some cases, the external surface of cover 200 may include additional one or more three dimensional objects that project out from the surface of the cover (for example, cartoon figures that project off the top 210 or front wall 202 or other themed shapes or objects).

In some embodiments, the underside of top 210 of cover 200 can have cover magnet 214, which may be held in place by cover magnet base 216, as illustrated in FIG. 18. Further, as illustrated in FIG. 1, cover magnet 214 can align with touch latch assembly 146 such that if a portion of the touch latch assembly, such as latch extension 150, is magnetic, the cover magnet can ensure that cover 200 stays attached to housing 100 when the flosser dispenser is picked up by the cover.

In other embodiments, cover 200 may have additional features such as, but not limited to, a scent or a scent production mechanism, a solar cell if the cover or housing 100 host electronics (such as a clock, radio, etc.), and it may be configured to generate a sound when it is opened in order to alert the user that the device is open and also to act as a positive reinforcement to encourage users to continue flossing.

Further, flosser dispenser can have additional augmentations to those described above. In one embodiment, flosser dispenser can be partially or entirely transparent (for example: the cover, the door, or a window in either of the cover or door may allow a user to see how many flossers remain). In another embodiment, flosser dispenser may be comprised of two or more dispensers that are connected by a single multi-state actuator (for example, four dispensers may be arranged in a circle with a single multi-state actuator in the center). In a further embodiment, the flosser dispenser may include ingress protection so that the dispenser can be kept in a shower or other area that is frequently splashed by water.

In some embodiments, the disclosed device is structured and configured to dispense objects other than flossers, such as food (in which case the dispenser could be insulated) or other disposable goods. Examples include, but are not limited to, gum, makeup remover pads, makeup sponges, coins, cotton swabs, batteries, soap bars, custom cookies, sponges, bath markers, candy, toilet paper, disposable contacts, razor heads, detergent pods, bath salt pellets, dry and/or rigid foods (for example, crackers, cookies, dog treats, etc.), powdered pellets (for example, antacids, dietary supplements, mosquito pellets, etc.), individually wrapped items (for example, contact lenses, wet wipes, etc.), and elongate objects (for example, pencils, pens, straws, etc.). If combined with ingress protection, some objects, like soap bars and razor heads, could be stored in a shower until they are needed for use, thereby freeing up other storage space in the bathroom and keeping those objects close to the location where they will be needed. In yet another embodiment, the cover of flosser dispenser may, instead of covering dispensing body 101, cover a hidden drawer that is used to hide small objects (i.e., the dispenser is designed to blend into its surroundings and isn't obviously a dispenser).

While flosser dispenser has been described herein as having top and bottom features, these features are not limited to those orientations and, upon rotating the flosser dispenser between right-handed and left-handed configurations, top features may be positioned beneath bottom features and vice versa. The ambidextrous nature of the dispenser enables it to be used easily by both right- and left-handed individuals or placed in locations that are more accessible from one side of the device or another.

Persons of ordinary skill in arts relevant to this disclosure and subject matter hereof will recognize that embodiments may comprise fewer features than illustrated in any individual embodiment described by example or otherwise contemplated herein. Embodiments described herein are not meant to be an exhaustive presentation of ways in which various features may be combined and/or arranged. Accordingly, the embodiments are not mutually exclusive combinations of features; rather, embodiments can comprise a combination of different individual features selected from different individual embodiments, as understood by persons of ordinary skill in the relevant arts. Moreover, elements described with respect to one embodiment can be implemented in other embodiments even when not described in such embodiments unless otherwise noted. Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended. Furthermore, it is intended also to include features of a claim in any other independent claim even if this claim is not directly made dependent to the independent claim.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of Section 112, sixth paragraph of 35 U.S.C. are not to be invoked unless the specific terms "means for" or "step for" are recited in a claim.

What is claimed is:

1. A flosser dispenser for dispensing individual flossers, the flosser dispenser comprising:
 a housing comprising:
  a dispensing body configured to house flossers in a stacked orientation, wherein the dispensing body includes a top cavity that is open at a top of the dispensing body, and
  a multi-state actuator structured to alternate between various states, including at least a compressed position and an extended position, wherein the multi-state actuator is housed within the top cavity; and
 a cover having an open bottom end that is structured and configured to fit over and around the housing, the cover having an interior shape larger than an exterior shape of the housing;
 wherein:
  the multi-state actuator in its compressed position allows the cover to substantially encompass the housing,
  the multi-state actuator in the extended position causes the cover to expose a portion of the housing such that at least one flosser is exposed, and the housing is structured and configured to allow no more than one flosser to be removed at a time when the multi-state actuator is in the extended position.

2. The flosser dispenser of claim 1, wherein:
the multi-state actuator is a bi-state actuator; and
an interior top surface of the cover is in contact with the multi-state actuator in both the compressed position and the extended position.

3. The flosser dispenser of claim 1, the dispensing body further comprising a bottom cavity that is open at a bottom of the dispensing body and is structured and configured to house the multi-state actuator.

4. The flosser dispenser of claim 3, wherein the top cavity and the bottom cavity are one continuous cavity.

5. The flosser dispenser of claim 3, wherein:
the cover is removable; and
the multi-state actuator is housed in one of the top cavity or the bottom cavity, thereby enabling the dispenser to be used in a right-handed or a left-handed position.

6. The flosser dispenser of claim 1, wherein the dispensing body includes a front face having at least a portion that is open to an interior of the dispensing body.

7. The flosser dispenser of claim 6, further comprising a door that covers at least a portion of the open front face of the dispensing body.

8. The flosser dispenser of claim 7, wherein the door is comprised of:
a vertical side portion that extends from a top of the open front face to a bottom of the open front face, therein covering at least a portion of each flosser in the dispensing body;
a horizontal side portion that extends from an interior edge of the vertical side portion across the open front face, wherein the horizontal side portion is centered on the interior edge of the vertical side portion; and
a door hinge that enables the door to open and close for loading of flossers.

9. The flosser dispenser of claim 8, wherein the horizontal side portion has a height that is less than the height of the open front face.

10. The flosser dispenser of claim 7, wherein:
the dispensing body further includes an interior back wall having a bottom layer interior groove aligned with a bottommost flosser; and
the interior groove is sized to enable a portion of a bottommost flosser to rotate from a stored position in the dispensing body through the groove so the bottommost flosser can be removed from the housing.

11. The flosser dispenser of claim 10, wherein each of the flossers are comprised of:
a head having a short prong and a long prong;
a handle attached to the head;
floss attached between the short prong and the long prong.

12. The flosser dispenser of claim 11, wherein:
the interior back wall aligns with flossers along the handle and the short prong;
the bottom layer interior groove aligns with the short prong; and
the dispensing body further comprises:
an interior side wall that aligns with the flosser heads such that the interior side wall is parallel to the floss,
a top interior surface, and
a bottom interior surface.

13. The flosser dispenser of claim 12, wherein:
the dispensing body further comprises a bottom cavity that is open at a bottom of the dispensing body and is structured and configured to house the multi-state actuator;
the multi-state actuator is housed in one of the top cavity or the bottom cavity, thereby enabling the dispenser to be used in a right-handed or a left-handed position; and
the dispensing body further comprises a top layer interior groove that is a mirror image of the bottom layer interior groove.

14. The flosser dispenser of claim 13, wherein a topmost flosser aligns with the top layer interior groove when the flosser dispenser is in the left-handed position.

15. The flosser of claim 1, wherein the multi-state actuator is a spring activated touch latch assembly comprising a latch base and a latch extension.

16. The flosser dispenser of 15, further comprising:
a removable top cap having:
a securing mechanism to attach the top cap to one of the top or a bottom of the dispensing body, and
an opening structured and configured to retain the latch base while allowing the latch extension to protrude through the opening; and
a removable base having:
a securing mechanism to attach the base to the other of the top or the bottom of the dispensing body.

17. A flosser dispenser for dispensing individual flossers, the flosser dispenser comprising:
a housing comprising:
a dispensing body configured to house flossers in a stacked orientation, wherein the dispensing body includes:
a top cavity that is open at a top of the dispensing body,
a bottom cavity that is open at a bottom of the dispensing body,
a front face having at least a portion that is open to an interior of the dispensing body, and
an interior back wall having a bottom layer interior groove and a top layer interior groove,
a door covering at least a portion of the open front face of the dispensing body;
a multi-state actuator structured to alternate between at least a compressed and an extended position, wherein the multi-state actuator is housed within the top cavity; and
a cover having an open bottom end that is structured and configured to fit over and around the housing, the cover having an interior shape larger than an exterior shape of the housing;
wherein:
the multi-state actuator is housed in one of the top cavity or the bottom cavity, thereby enabling the dispenser to be used in a right-handed or a left-handed position,
the multi-state actuator, in the compressed position, allows the cover to substantially encompass the housing,
the multi-state actuator, in the extended position, causes the cover to expose a portion of the housing such that a plurality of flossers are exposed, and
the housing is structured and configured to allow no more than one flosser to be removed at a time when the multi-state actuator is in the extended position.

18. The flosser dispenser of claim 17, wherein:
the bottom layer interior groove is sized to enable a portion of a bottommost flosser to rotate from its stored position in the dispensing body through the groove so the bottommost flosser can be removed from a bottom end of the housing;
the top layer interior groove is sized to enable a portion of a topmost flosser to rotate from its stored position in the dispensing body through the groove so the topmost flosser can be removed from a top end of the housing;
the dispensing body further comprises:
  a first side;
  a second side;
  a top interior surface;
  a bottom interior surface;
  a top wedge cutout on a front corner of a top end of the second side that is structured and configured to expose the handle of at least one flosser and is horizontally aligned with the top interior surface such that a top portion of the top wedge cutout is above a plane of the top interior surface and a bottom portion of the top wedge cutout is below the plane of the top interior surface;
  a bottom wedge cutout on a front corner of a bottom end of the second side that is structured and configured to expose the handle of at least one flosser and is horizontally aligned with the bottom interior surface such that a top portion of the bottom wedge cutout is above a plane of the bottom interior surface and a bottom portion of the bottom wedge cutout is below the plane of the bottom interior surface.

19. The flosser dispenser of claim 18, wherein:
a top half and a bottom half of the dispensing body along a horizontal plane are mirror images of each other and allow the dispenser to dispense from either the top end or the bottom end; and
the interior configuration of the dispensing body retains the flossers in the dispensing body in a stacked orientation and prevent extraction of more than one flosser at a time.

20. A method of using a flosser dispenser, the method comprising:
  pressing a cover down to engage a bi-state actuator;
  releasing engagement with the cover to move the cover into an activated configuration and expose a portion of a dispensing body, the dispensing body being structured and configured to fit substantially within the cover when the cover is in a closed configuration; and
  pulling a tail edge of a flosser forward through a first wedge cutout on a front corner of a bottom end of the dispensing body;
wherein:
  a bottom layer interior groove carved into an interior back wall near a back corner of the bottom end of the dispensing body permits a portion of a flosser head of the flosser to rotate through the interior back wall for removal;
  the bottom layer interior groove is sized to permit no more than one flosser head to rotate through at a time; and
  a door on a front face of the dispensing body prevents the flosser from falling out when the cover is in the activated configuration or when the cover is removed from the dispensing body.

* * * * *